United States Patent [19]

Celmer et al.

[11] 4,195,079
[45] Mar. 25, 1980

[54] NEW POLYCYCLIC ETHER ANTIBIOTIC

[75] Inventors: Walter D. Celmer, New London; Walter P. Cullen, East Lyme; John R. Oscarson, Pawcatuck; Liang H. Huang, East Lyme, all of Conn.; Riichiro Shibakawa, Handa; Junsuke Tone, Chita, both of Japan

[73] Assignee: Pfizer Inc., New York, N.Y.

[21] Appl. No.: 7,901

[22] Filed: Jan. 31, 1979

[51] Int. Cl.$^2$ ............................................. A61K 35/00
[52] U.S. Cl. .................................... 424/122; 435/825; 435/132
[58] Field of Search ........................... 424/122; 195/81

[56] References Cited

U.S. PATENT DOCUMENTS 4,132,778   1/1979   Hamill et al. ......................... 424/122

*Primary Examiner*—Jerome D. Goldberg
*Attorney, Agent, or Firm*—Connolly and Hutz

[57] ABSTRACT

A new polycyclic ether antibiotic produced by a strain of *Actinomadura verrucosospora* under submerged fermentation conditions is useful in controlling coccidiosis in poultry and in improving feed utilization efficiency in ruminants.

6 Claims, 2 Drawing Figures

Infrared Absorption Spectrum Of Free Acid Of Compound 51,532

Infrared Absorption Spectrum Of Sodium Salt Of Compound 51,532

NEW POLYCYCLIC ETHER ANTIBIOTIC

BACKGROUND OF THE INVENTION

This invention is concerned with a new member of the acidic polycyclic ether group of antibiotics, a class of compounds characterized biologically by their effect on cation transport in mitochondria. This family of antibiotics includes monensin (J. Amer. Chem. Soc., 89:5737, 1967); nigericin (Biochem. Biophys. Res. Comm., 33:29, 1968); grisorixin (J. Chem. Soc. Commun., 1421, 1970); dianemycin (J. Antibiotics, 22:161, 1969); salinomycin (J. Antibiotics, 27:814, 1974); X-537A (J. Chem. Soc. Chem. Commun., 967, 1972); X-206 (J. Chem. Soc. Chem. Commun., 927, 1971); and A204A (J. Amer. Chem. Soc., 95:3399, 1973).

The polycyclic ether antibiotics listed above are active against Gram-positive bacteria, fungi and protozoa. These antibiotics exhibit potent anticoccidial activity.

The control of coccidiosis continues to be a serious problem to the poultry industry. There are six species of coccidia which produce easily discernible morbidity in susceptible chickens, *Eimeria tennella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively inocuous; however, *E. mitis, E. hagani* and *E. praecox* are capable of reducing weight gain, lowering feed efficiency and adversely affecting egg production.

SUMMARY OF THE INVENTION

This invention is concerned with a new polycyclic ether antibiotic produced by a new strain of *Actinomadura verrucosospora* Nonomura and Ohara under submerged aerobic conditions in aqueous nutrient media. Antibiotic Compound 51,532 and its cationic salts are active against a variety of microorganisms, effective in controlling coccidiosis in poultry and act to improve feed utilization efficiency in ruminants.

DETAILED DESCRIPTION OF THE INVENTION

Figure 1:
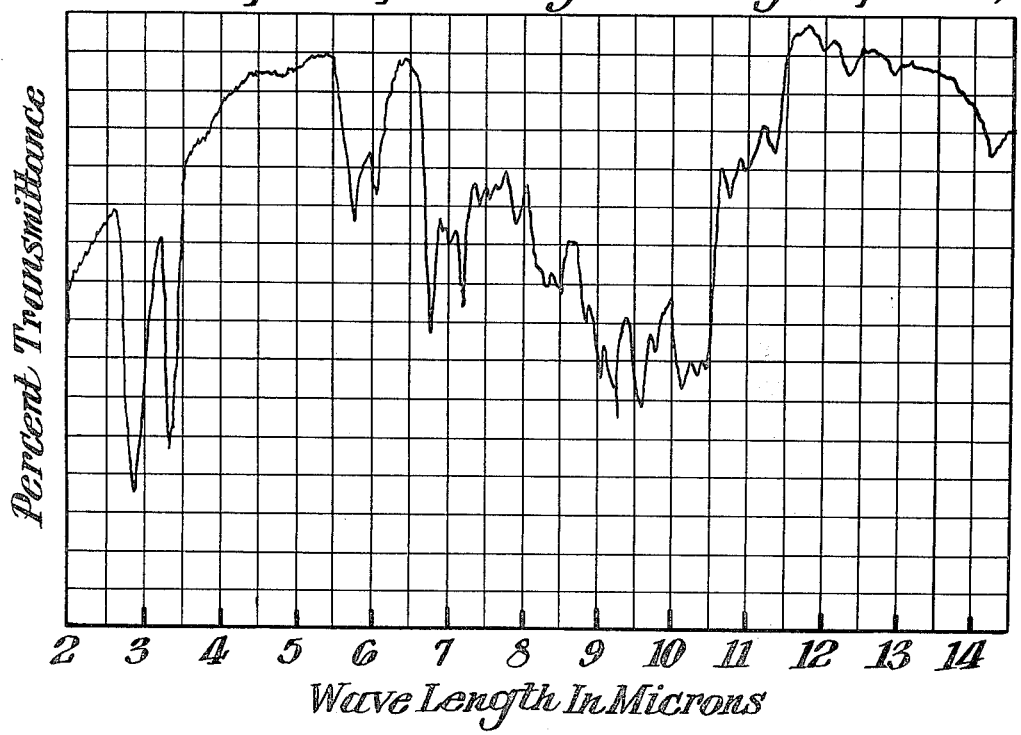

The antibiotic producing microorganism of the present invention, isolated from a soil sample in India, was found on examination to have narrow hyphae of the Actinomycetales and aerial mycelium with short spore chains characteristic of members of the genus Actinomadura.

The culture was planted from a freeze-dried vial in liquid ATCC 172 medium and grown for 3 days at 28° C. on a shaker. It was then removed from the shaker, centrifuged for 20 minutes, washed three times with sterile distilled water and planted on media commonly used for identification of members of the Actinomycetales.

Incubation was conducted at 28° C. Readings of results were made at different times but most final results were recorded at the end of 15 days. The colors were described in common terminology but exact colors were determined by comparison with color chips from the Color Harmony Manual, fourth edition. The methods of whole-cell and sugar analyses are those described by Becker, B. et al., Appl. Microbiol., 12, 421-423 (1964); and Lechevalier, M.P. et al., J. Lab. Clin. Med., 71, 934-944 (1968).

For comparison purposes, type strains of cultures of *Actinomadura citrea* ATCC 27887 and *Actinomadura verrucosospora* ATCC 27299 were used.

Identification media used for the characterization of the culture and reference for their composition are as follows:

1. Trypton Yeast Extract Broth—(ISP #1 medium, Difco).
2. Yeast-Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Tyrosine Agar—(ISP #7 medium, Difco).
8. Czapek-Sucrose Agar—S. A. Waksman, The Actinomycetes, Vol. 2, medium no. 1, p. 328, 1961.
9. Glucose Asparagine Agar—Ibid, medium no. 2, p. 328.
10. Bennett's Agar—Ibid, medium no. 30, p. 331.
11. Emerson's Agar—Ibid, medium no. 28, p. 331.
12. Nutrient Agar—Ibid, medium no. 14, p. 330.
13. Gordon and Smith's Tyrosine Agar—R. E. Gordon and M. M. Smith, Jr. Bact. 69:147-150, 1955.
14. Casein Agar—Ibid.
15. Calcium Malate Agar—S. A. Waksman, Bact. Rev. 21:1-29, 1957.
16. Gelatin—R. E. Gordon and J. M. Mihm, Jr. Bact. 73:15-27, 1957.
17. Starch—Ibid.
18. Organic Nitrate Broth—Ibid.
19. Dextrose Nitrate Broth—S. A. Waksman, The Actinomycetes, Vol 2, medium no. 1, p. 328, 1961, with 3 g dextrose substituted for 30 g sucrose and agar omitted.
20. Potato Carrot Agar—M. P. Lechevalier, J. Lab. and Clinical Med. 71:934-944, 1968 but use only 30 g potatoes, 2.5 g carrots and 20 g agar.
21. 2% Tap Water Agar.
22. Gauze's 1% Mineral Agar—G. F. Gauze et al., Problems in the Classification of Antagonistic Actinomycetes. English Ed., p. 13, 1957.
23. Gauze's #2 Organic Agar—Ibid.
24. Skim Milk—Difco.
25. Cellulose utilization—
 (a) H. L. Jensen, Proc. Linn. Soc. N.S.W. 55:231-248, 1930.
 (b) M. Levine and H. W. Schoenlein, A Compilation of Culture Media, medium no. 2511, 1930.
26. Carbohydrates—ISP #9 medium, Difco., with addition of glycerol and melibiose as carbon sources.
27. Temperature Range—ATCC medium 172 in ATCC Culture Collection Catalogue, 12th ed. p. 329, 1976.

The culture was described as follows on the various media:

Yeast Extract-Malt Extract Agar—Growth good, pale bluish (14 ca to 14 da), raised, wrinkled to rarely furrowed, with pale bluish aerial mycelium; reverse pinkish orange to greyish blue (5 ia to 15 li); soluble pigment very pale yellowish brown, but becoming pale bluish after 4 weeks of incubation.

Oatmeal Agar—Growth moderate, bluish (15 ca to 15 ea), thin, smooth, with bluish aerial mycelium; reverse pale bluish to pinkish (5 ea); no soluble pigment.

Inorganic Salts-Starch Agar—Growth good, pale lavender (5 ec) to greyish blue (15 ge to 15 ig) with a pinkish orange (near 5 ic) edge, thin, smooth to slightly wrinkled, aerial mycelium sparse, white; reverse pale lavender to pinkish orange (5 gc, 6 ga to 6 ia); no soluble pigment. After 4 weeks on incubation, the colonies became greyish blue with a reddish orange to reddish edge, the aerial mycelium was greyish blue and more abundant, and very pale bluish soluble pigment was produced.

Glycerol-Asparagine Agar—Growth poor to moderate, pale bluish (close to near grey series 19 ba), thin, smooth, with pale bluish aerial mycelium; reverse cream to pale pinkish; no soluble pigment.

Gordon and Smith's Tyrosine Agar—Growth good, pale pinkish orange to pale pinkish grey (5 ea to 5 gc) with white periphery, raised, smooth but wrinkled toward the edge, no aerial mycelium; reverse same as surface; soluble pigment pinkish orange (5 ic).

Czapek-Sucrose Agar—Growth moderate, cream (near 2 ca), thin, smooth, no aerial mycelium; reverse same as surface; no soluble pigment.

Glucose-Asparagine Agar—Growth good, pinkish orange (5 ea to 5 ga), slightly raised, smooth to wrinkled, with white aerial mycelium; reverse same as surface; no soluble pigment.

Calcium Malate Agar—Growth poor to moderate, colorless, thin, smooth aerial mycelium absent or rudimentary; reverse colorless; no soluble pigment.

Casein Agar—Growth moderate to good, pale pinkish (5 ca to 5 ea), moderately raised, slightly wrinkled, no aerial mycelium; reverse same as surface; no soluble pigment.

Bennett's Agar—Growth excellent, pale bluish, pale pinkish to bluish grey (15 ca, 7 ca, to 13½ ig), raised, roughened to wrinkled, with pale bluish aerial mycelium; reverse pale yellowish pink to pale yellowish grey (4 ea to 3 ge); no soluble pigment.

Emerson's Agar—Growth good, white, raised, wrinkled, with white aerial mycelium; reverse colorless; no soluble pigment.

Nutrient Agar—Growth moderate to good, pale pinkish ( 5 ca), thin to slightly raised, smooth, with white aerial mycelium; reverse pale yellowish orange (4 ea); no soluble pigment.

Gelatin Agar—Growth good, pale orange (3 ea), raised, wrinkled, no aerial mycelium; reverse same as surface; no soluble pigment.

Starch Agar—Growth good, pale orange to pale pinkish orange (4 ea to 5 ea), raised, smooth but wrinkled toward edge, no aerial mycelium; reverse same as surface; no soluble pigment.

Potato Carrot Agar—Growth moderate, pale pinkish to pale bluish (5 ca, 5 ea, to 14 ca), thin, smooth, with pale bluish aerial mycelium; reverse pinkish (6 ea); no soluble pigment.

Tap Water Agar—Growth poor, colorless to pale white, thin, smooth, with rudimentary, white aerial mycelium; reverse colorless; no soluble pigment.

Gauze's #1 Mineral Agar—Growth moderate, cream (near grey series 1 ba), thin to slightly raised, smooth, with no to sparse white aerial mycelium; reverse same as surface; no soluble pigment.

Gauze's #2 Organic Agar—Growth good, pale yellowish (2 ea), pale pinkish to orange red (5 ea, 5 na to 5 pa), raised wrinkled, with white aerial mycelium; reverse orange (5 ia); no soluble pigment.

Biochemical Properties—Melanin not produced; hydrogen sulfide not produced; gelatin liquefied; starch hydrolyzed; nitrate reduced to nitrite on both media; very poor growth on Jensen's cellulose, no growth on Levine and Schoenlein's cellulose, no decomposition on both cellulose media; clearing but no coagulation on milk; casein digestion negative; no digestion of calcium malate; tyrosine digestion positive. Carbohydrate utilization: glucose, arabinose, fructose, glycerol, mannitol, rhamnose, sucrose, and xylose utilized; inositol doubtfully utilized; melibiose and raffinose not utilized.

Morphological Properties—Spore chain morphology was observed on yeast extract-malt extract agar, oatmeal agar, and inorganic salts-starch agar. Spore chains straight, curved, hooked, looped, or coiled in one turn, 1 to 9 (mostly 3 to 6) spores per chain; spores bluish in mass. The following morphological observations were made on the 15-day-old culture grown on oatmeal agar: Sporophores produced monopodially, often crowded giving the appearance of isolated patches, warty, globose to oval, rarely elliptical, 1–1.3 $\mu$m, or 1.2–1.6(−2.0)×1–1.2 $\mu$m.

Temperature Relations—

| 21° C. | 28° C. | 37° C. | 45° C. |
|---|---|---|---|
| good growth | excellent growth | excellent growth | good growth |

Cell Wall Analysis—The cell wall contains meso-diaminopimelic acid, madurose, and glucose.

The culture is characterized by pale bluish aerial mycelium, pale pinkish or pale orange colony reverse and short spore chains with warty spores. These features, coupled with the presence of meso-diaminopimelic acid and madurose in the cell wall, place the culture in the genus Actinomadura. When compared with the two known species of Actinomadura, the culture most resembles *Actinomadura verrucosospora* Nonomura and Ohara in cultural and morphological characteristics. It has the same pattern of carbohydrate utilization and other physiological characteristics as those of *Actinomadura verrucosospora* except that it can reduce nitrate and does not coagulate milk, whereas the reverse is true for the latter organism. Thus, the new culture is considered to be a new strain of *Actinomadura verrucosospora*. It has been deposited at The American Type Culture Collection with the accession number ATCC 31466.

The permanency of the deposit of this culture at The American Type Culture Collection in Rockville, Md. and ready accessibility thereto by the public are afforded in the event the patent is granted. Access to the culture is available during pendency of the application under Rule 14 and 35 USC 112. All restrictions on the availability to the public of the culture deposited will be irrevocably removed upon granting of the patent.

Cultivation of the culture *Actinomadura verrucosospora* ATCC 31466 preferably takes place in aqueous nutrient media at a temperature of 28°–36° C., and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 3 to 5 days whereas inoculum in submerged inoculum tanks will usually be at the most favorable period in 3 to 4 days. Substantial antibiotic activity is obtained in the final fermentor stage in approximately 3 to 5 days. The antibiotic levels range from 50 to 500 mg per liter.

The process of antibiotic production is conveniently followed during fermentation by biological assay of the broth employing a sensitive strain of *Staphylococcus aureus* or *Bacillus subtilis*. Standard plate assay technique is employed in which the zone of inhibition surrounding a filter paper disc saturated with the broth is used as a measure of antibiotic potency.

Thin-layer chromatography employing silica gel is a useful tool for analyzing the antibiotic produced in fermentation media and the composition of crude and purified materials extracted from the fermentation broths. The Analtech silica gel GF chromatograms are developed with ethyl acetate. Antibiotic Compound 51,532 is visualized by spraying with 3% vanillin in ethanolic sulfuric acid (97:3 v/v). It shows up as a reddish orange spot on a white background on warming on a steam bath or a hot plate. Bio-overlay with agar seeded with a sensitive strain of *Staphylococcus aureus* or *Bacillus subtilis* is a further procedure for detection of the antibiotic.

The antibiotic may be separated and recovered by extracting the whole, unfiltered fermentation broth with an organic solvent such as chloroform, ethyl acetate, methylisobutyl ketone or butanol at a pH range of 4.0 to 10.0. A major portion of the antibiotic activity is contained in the mycelium and may be extracted therefrom by slurrying the separated mycelium with a water-soluble solvent such as methanol. The solvent is concentrated to a thin syrup.

A method of separation and recovery of antibiotic Compound 51,532 is as follows: Whole *Actinomadura verrucosospora* ATCC 31466 fermentation broth is extracted with methylisobutyl ketone. The solvent extract is evaporated under vacuum to a dark oil. The oil is dissolved in chloroform and poured onto a bed of silica gel contained in a sintered glass funnel. The silica gel bed is washed successively with chloroform, ethyl acetate and acetone. Antibiotic Compound 51,532, as demonstrated by thin-layer chromatography, is found almost exclusively in the ethyl acetate fraction. This fraction, after evaporation to dryness, is taken up in ethyl acetate-heptane (3:1) and added to a column packed with silica gel slurried in ethyl acetate-heptane (3:1) and eluted with the same solvent system. Column cuts containing Compound 51,532, as determined by thin-layer chromatography, are combined, evaporated to a small volume and then washed with 5% w/v monosodium phosphate buffer adjusted to pH 4.5 with phosphoric acid. The solvent phase is then washed with 5% w/v disodium phosphate buffer the pH of which was adjusted to 9.0 with sodium hydroxide solution. The solvent phase is then dried over anhydrous sodium sulfate and taken to dryness. The residue is dissolved in methanol and placed in the refrigerator or chilled in ice whereupon Compound 51,532 crystallizes as the sodium salt. The free acid may be obtained by washing an ethyl acetate solution of the sodium salt with water adjusted to pH 4.5. Concentration of the solvent phase under vacuum affords the amorphous free acid of Compound 51,532.

Antibiotic Compound 51,532 exhibits inhibitory action against the growth of a number of Gram-positive microorganisms. The compound and its cationic salts exhibit excellent activity against coccidial infections in poultry. When incorporated into the diet of chickens at levels of 75 to 150 ppm, these compounds are effective in controlling infections due to *Eimeria tenella, E. acervulina, E. maxima, E. brunetti* and *E. necatrix*.

Efficacy data for Compound 51,532 and its cationic salts against coccidial infections in chickens were obtained as follows: Groups of 3–5 ten-day-old SPF white leghorn cockerel chicks were fed a mash diet containing antiobiotic Compound 51,532 or its sodium and/or potassium salt uniformly dispersed therein. After being on this ration for 24 hours, each chick was inoculated per os with oocysts of the particular species of Eimeria being tested. Other groups of 3–5 ten-day-old chicks were fed a similar mash diet free from antiobiotic Compound 51,532 or its salts. They were also infected after 24 hours and served as infected controls. Still other groups of chicks were fed the mash diet free of antibiotic Compound 51,532 and were not infected with the coccidia. These served as normal controls. The results of treatment were evaluated after five days in the case of *E. acervulina* and six days for all other challenges.

| Species Infections | Dose (ppm) | Avg. degree[1] of infection | Ratio | Weight gain(%) |
|---|---|---|---|---|
|  | 150 (2) | 1.7 (0.3) | 0.54 (0.1) | 82 (22) |
| E. tenella | 100 (2) | 0.0 (0.7) | 0.00 (0.23) | 54 (70) |
|  | 75 — | —(0.7) | — (0.23) | —(67) |
|  | 150 | 1.2 | 0.60 | 7 |
| E. acervulina | 100 | 1.8 | 0.90 | 30 |
|  | 75 | 2.0 | 1.0 | 25 |
| E. necatrix | 150 | 1.2 | 0.46 | 30 |
|  | 100 | 0.8 | 0.31 | 19 |
| E. maxima | 150 | 0.2 | 0.08 | 0 |
|  | 100 | 0.4 | 0.17 | 13 |
| E. brunetti | 150 | 0.2 | 0.08 | 38 |
|  | 100 | 0.6 | 0.23 | 42 |

[1] The criteria used to measure anticoccidial activity consisted of lesion scores of 0 to 4 for E. tenella after J. E. Lynch (1961). A new method for the primary evaluation of anticoccidial activity. Am. J. Vet. Res. 22:324–326); and 0 to 3 for the other species based on a modification of the scoring system devised by J. Johnson and W. H. Reid (1970. Anticoccidial drugs. Lesion scoring techniques in batter and floor pen experiments in chicks. Exp. Parasit. 28:30–36). A constant ratio was established by dividing the lesion score of each treated group by the lesion score of the infected control.

The value of animal feeds generally has been determined directly by feeding the animal. G.B. No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg. of standard substrate (68% corn starch + 17% cellulose + 15% extracted soybean meal), b 10 ml of a pH 6.8 buffer and the test compound. The flasks are gassed with oxygen free nitrogen for about two minutes, and incubated in a shaking water bath at 39° C. for about 16 hours. All tests are conducted in triplicate.

After incubation 5 ml of the sample are mixed with 1 ml of 25% metaphosphoric acid. After 10 minutes 0.25 ml of formic acid is added and the mixture centrifuged at 1,500 r.p.m. for 10 minutes. Samples are then analyzed by gas-liquid chromatography by the method for D. W. Kellog in J. Dairy Science 52, 1690 (1969). Peak heights for acetic, propionic and butyric acids are determined for samples from untreated and treated incubation flasks.

When tested by this in vitro procedure, the sodium salt of Compound 51,532 (20 ppm) gave rise to greater than 50% increase in the production of propionic acid over that product in the control solution without added Compound 51,532. Similar results may be obtained with other pharmaceutically acceptable salts or the free acid.

Based on this data, it can be projected that improvement of feed utilization by ruminants such as cattle and sheep and monogastric animals such as horses, pigs and rabbits will be comparable with that obtained by commercially available Monensin, a polycyclic ether antibiotic. Antiobiotic Compound 51,532 may be incorporated in feed compositions as the free acid, sodium salt, potassium salt or mixtures thereof. Crude forms of Compound 51,532 or dried fermentation broth containing the antibiotic may be incorporated in feed compositions at the desired potency concentrations.

EXAMPLE I

A sterile aqueous medium having the following composition was prepared:

| Ingredient | Grams/liter |
| --- | --- |
| Glucose | 10 |
| Starch | 20 |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |

-continued

| Ingredient | Grams/liter |
| --- | --- |
| pH 7.1-7.2 | |

Cells from a slant of *A. verrucosospora* ATCC 31466 were transferred to a series of 300 ml flasks each containing 50 ml of this sterile medium and shaken on a rotary shaker at 28°-30° C. for 3-4 days. An aliquot of the grown culture, sufficient to provide a 5% v/v inoculum, was transferred to four liter fermentors each containing two liters of the following sterile medium:

| Ingredient | Grams/liter |
| --- | --- |
| Glucose | 20 |
| Soy flour | 30 |
| Ferric sulfate | 0.3 |
| Manganese chloride | 0.3 |
| Cobalt chloride | 0.002 |
| pH 6.9-7.1 | |

The fermentation was conducted at 28°-36° C. with stirring at 1700 revolutions per minute and aeration at 1.5 to 2 volumes of air per volume of broth per minute until substantial activity was obtained (48-120 hours). The whole broth, without pH adjustment, was twice extracted with ⅓ to ½ volume of methylisobutyl ketone. The separated solvent extracts were combined and concentrated under vacuum to a thin syrup.

EXAMPLE 2

The inoculum medium of Example 1 was distributed in 700 ml amounts in 4 to 8 shake flasks and inoculated with cells of *A. verrucosospora* ATCC 31466. After incubation at 28° C. on a rotary shaker for 3 to 8 days, a 3 to 5% v/v inoculum was introduced into a 50 gallon fermentor containing twenty five gallons of the following sterile medium:

| Ingredient | Grams/liter |
| --- | --- |
| Glucose | 1 |
| Soy flour | 10 |
| Corn starch | 10 |
| Grain solubles | 5 |
| Ferric sulfate | 0.2 |
| Manganese chloride | 0.2 |
| Cobalt chloride | 0.002 |
| Sodium chloride | 5 |
| Methyl oleate | 2 |
| Calcium carbonate | 1 |
| Soybean oil | 2 |
| pH 6.9-7.1 | |

The fermentation was conducted for a period of 5 days at 30° C. with an aeration rate of one volume of air per volume of medium per minute.

One thousand gallons of whole broth, without pH adjustment, was extracted with ⅓ volume methylisobutyl ketone. The solvent extract was evaporated under vacuum to give approximately 700 grams of a dark oil.

The 700 grams of oil was dissolved in chloroform and poured into a bed of 2.5 kg of column grade silica gel 60 (E. Merck, Darmstadt, Germany) contained in a large sintered glass funnel. The silica gel was then washed successively with 5 gallons each of chloroform, ethyl acetate and acetone. These fractions were examined by thin-layer chromatography and antibiotic Compound 51,532 was found almost exclusively in the ethyl acetate fraction. This fraction was evaporated to dryness (220 grams).

The concentrate was further purified by column chromatography. A 80 mm×1 m column was packed with column grade silica gel 60 slurried in ethyl acetate-heptane (3:1). A portion of the concentrate (110 grams) was applied to the column in solution in ethyl acetate-heptane (3:1) and eluted with same solvent system. The column was run at 60 ml/minute and 1 liter cuts were taken. Progress of the column was followed by thin-layer chromatography. Following completion of the chromatography, the column was washed with heptane and the remaining 110 grams of concentrate was processed in the same manner.

Cuts from both columns containing Compound 51,532 were combined and evaporated to approximately 500 ml, and then washed with 500 ml of a 5% monosodium phosphate buffer solution adjusted to pH 4.5 with 85% w/v phosphoric acid. The solvent phase was washed with 500 ml of a 5% w/v disodium phosphate buffer solution the pH of which was adjusted to 9.0 with 1 N sodium hydroxide. The solvent phase was dried over anhydrous sodium sulfate and evaporated to dryness. The residue was taken up in methanol and allowed to crystallize in the refrigerator. Crystals were collected by filtration and dried under high vacuum at room temperature to yield 13.7 grams of Compound 51,532 as the sodium salt, m.p. 199°–204° C.

Figure 2:
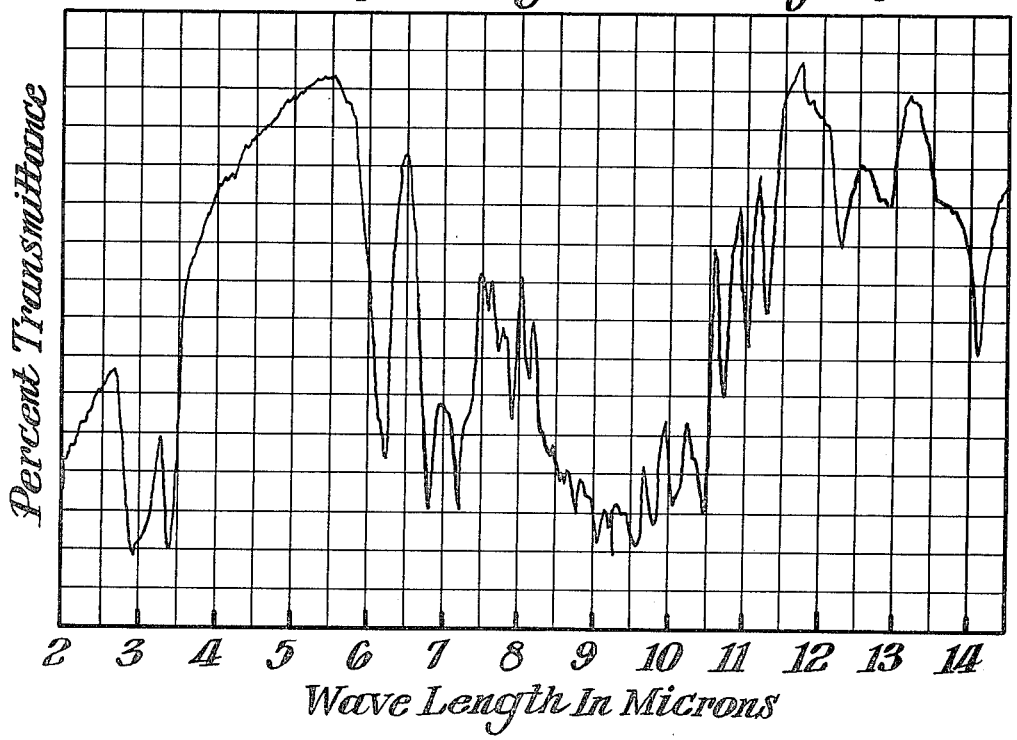

The sodium salt of Compound 51,532 is soluble in chloroform, ethyl acetate, acetone and methylisobutyl ketone; it is insoluble in water. The sodium salt is characterized by an average composition by weight of 62.17% carbon and 8.75% hydrogen; an optical rotation of $[a]_D^{25} = -29.9°$ (c=1.0, chloroform; no ultraviolet light absorption spectrum; and when pelleted in KBr, distinguishable bands in the infrared region as shown in FIG. 2 at the following wavelengths in microns: 2.90, 3.40, 6.25, 6.82, 7.25, 7.95, 8.80, 9.10, 9.65, 9.85, 10.10, 10.50, 10.75, 11.08, 11.33, 12.32 and 14.15.

The free acid of Compound 51,532 was derived by washing an ethyl acetate solution of the sodium salt of Compound 51,532 with a pH 4.5 aqueous phase (water adjusted to pH 4.5 with 85% phosphoric acid). The solvent layer was evaporated under vacuum to dryness, m.p. 117°–132° C. The free acid of Compound 51,532 could not be induced to crystallize.

The free acid of Compound 51,532 is soluble in chloroform, ethyl acetate and methylisobutyl ketone; it is insoluble in water. The free acid is characterized by an average composition by weight of 62.88% carbon, 8.80% hydrogen and 28.37% oxygen (by difference); an optical rotation of $[a]_D^{25} = -11.0°$ (c=1.0, chloroform); no ultraviolet light absorption spectrum; and when pelleted in KBr, distinguishable bands in the infrared region as shown in FIG. 1 at the following wavelengths in microns: 2,88, 3.32, 5.75, 6.06, 6.80, 7.20, 7.90, 8.50, 9.03, 9.60, 10.12, 10.75 and 11.35.

What is claimed is:

1. The antibiotic Compound 51,532 when in the form as the free acid is soluble in chloroform, ethyl acetate and methylisobutyl ketone and insoluble in water; has a melting point of 117°–132° C.; an optical rotation of $[a]_D^{25} = -11.0°$ at a concentration of 1% in chloroform; an average composition by weight of 62.83% carbon, 8.80% hydrogen and 28.37% oxygen (by difference); and when pelleted in KBr, exhibits characteristic absorption in the infrared region at the following wavelengths in microns: 2.88, 3.32, 5.75, 6.06, 6.80, 7.20, 7.90, 8.50, 9.03, 9.60, 10.12, 10.75 and 11.35.

2. The antibiotic Compound 51,532 as defined in claim 1 when in the form of the cystalline sodium salt.

3. A process for producing antibiotic Compound 51,532 as defined in claim 1 which comprises cultivating the microorganism *Actinomadura verrucosospora* ATCC 31466 in an aqueous nutrient medium containing an assimilable source of carbon and nitrogen and inorganic salts until substantial antibiotic activity is obtained.

4. A process according to claim 3 wherein said antibiotic is separated from the fermentation medium.

5. A process according to claim 3 wherein the fermentation medium is taken to dryness.

6. The method of controlling coccidiosis in poultry which comprises administering to poultry an effective amount for controlling coccidiosis of antibiotic Compound 51,532 as defined in claim 1 incorporated in the diet of said poultry.

* * * * *